(12) United States Patent
Gerdts

(10) Patent No.: US 6,689,120 B1
(45) Date of Patent: Feb. 10, 2004

(54) REDUCED PROFILE DELIVERY SYSTEM

(75) Inventor: Michael D. Gerdts, Big Lake, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 09/632,863

(22) Filed: Aug. 4, 2000

Related U.S. Application Data (60) Provisional application No. 60/147,645, filed on Aug. 6, 1999.

(51) Int. Cl.[7] .............................................. A61M 25/00
(52) U.S. Cl. ...................................... 604/526; 604/527
(58) Field of Search ................................ 604/524, 525, 604/526, 527; 606/108, 194, 195; 623/1.11, 1.12

(56) References Cited

U.S. PATENT DOCUMENTS

| | | | |
|---|---|---|---|
| 243,396 A | 6/1881 | Pfarre | |
| 2,211,975 A | 8/1940 | Hendrickson | 128/349 |
| 2,437,542 A | 3/1948 | Krippendorf | 128/349 |
| 3,174,851 A | 3/1965 | Buehler et al. | 75/170 |
| 3,351,463 A | 11/1967 | Rozner et al. | 75/170 |
| 3,416,531 A | 12/1968 | Edwards | 128/348 |
| 3,753,700 A | 8/1973 | Harrison et al. | 75/175.5 |
| 3,757,768 A | 9/1973 | Kline | 128/2 M |
| 3,924,632 A | 12/1975 | Cook | 128/348 |
| 4,425,919 A | 1/1984 | Alston, Jr. et al. | 128/658 |
| 4,430,083 A | 2/1984 | Ganz et al. | 604/283 |
| 4,484,586 A | 11/1984 | McMickle et al. | 128/786 |
| 4,516,972 A * | 5/1985 | Samson | 604/282 |
| 4,547,193 A | 10/1985 | Rydell | 604/282 |
| 4,567,024 A | 1/1986 | Koyama et al. | 422/56 |
| 4,676,229 A | 6/1987 | Krasnicki et al. | 128/4 |
| 4,737,153 A | 4/1988 | Shimamura et al. | 604/282 |
| 4,739,768 A | 4/1988 | Engelson | 128/658 |
| 4,806,182 A | 2/1989 | Rydell et al. | 156/211 |
| 4,832,681 A | 5/1989 | Lenck | 600/34 |
| 4,899,787 A | 2/1990 | Ouchi et al. | 138/131 |
| 4,981,478 A | 1/1991 | Evard et al. | 604/282 |
| 4,994,069 A | 2/1991 | Ritchart et al. | 606/191 |
| 5,019,057 A | 5/1991 | Truckai | 604/282 |
| 5,026,377 A | 6/1991 | Burton et al. | 606/108 |
| 5,037,404 A | 8/1991 | Gold et al. | 604/282 |
| 5,057,092 A | 10/1991 | Webster, Jr. | 604/282 |
| 5,069,674 A | 12/1991 | Fearnot et al. | 604/282 |
| 5,122,136 A | 6/1992 | Guglielmi et al. | 606/32 |
| 5,176,660 A * | 1/1993 | Truckai | 604/282 |
| 5,178,158 A | 1/1993 | de Toledo | 128/772 |

(List continued on next page.)

FOREIGN PATENT DOCUMENTS

| | | | |
|---|---|---|---|
| DE | 3642107 | 12/1986 | A61B/1/00 |
| EP | 0098100 | 1/1984 | A61B/1/00 |

(List continued on next page.)

*Primary Examiner*—Sharon Kennedy
(74) *Attorney, Agent, or Firm*—Larkin Hoffman Daly & Lindgren Ltd.; Frederick W. Niebuhr, Esq.

(57) ABSTRACT

A catheter is formed with a layered wall construction including an inside tube formed of a low friction polymer, a polymeric outside tube, and a metallic reinforcement braid embedded in the wall between the inside and outside tubes. The braid is composed of multiple elongate flexible strands preferably of stainless steel, wound in two opposite directions and interbraided with one another. Each strand has a rectangular transverse profile, with a profile width at least three times the profile thickness. The strands are wound with their thicknesses directed radially of the catheter wall, permitting the catheter wall to be formed at a reduced thickness while maintaining favorable structural characteristics including pushability, torqueability, flexibility and resistance to kinking. As a result, the catheter's outside diameter can be reduced without reducing its interior lumen, or alternatively a larger interior lumen can be provided in a catheter of a given size.

20 Claims, 4 Drawing Sheets

U.S. PATENT DOCUMENTS

| | | | |
|---|---|---|---|
| 5,180,376 A | | 1/1993 | Fischell .................... 604/282 |
| 5,184,627 A | | 2/1993 | de Toledo ................. 128/772 |
| 5,217,482 A | | 6/1993 | Keith ........................ 606/194 |
| 5,221,270 A | | 6/1993 | Parker ....................... 604/282 |
| 5,222,949 A | | 6/1993 | Kaldany .................... 604/282 |
| 5,248,305 A | | 9/1993 | Zdrahala ................... 604/280 |
| 5,279,596 A | | 1/1994 | Castaneda et al. ......... 604/282 |
| 5,313,967 A | | 5/1994 | Lieber et al. .............. 128/772 |
| 5,336,205 A | | 8/1994 | Zenzen et al. ............. 604/280 |
| 5,338,295 A | * | 8/1994 | Cornelius et al. ............ 604/96 |
| 5,354,295 A | | 10/1994 | Guglielmi et al. ........... 606/32 |
| 5,364,357 A | | 11/1994 | Aase ............................ 604/96 |
| 5,403,292 A | | 4/1995 | Ju .............................. 604/282 |
| 5,405,338 A | | 4/1995 | Kranys ...................... 604/282 |
| 5,405,380 A | | 4/1995 | Gianotti et al. ................ 623/1 |
| 5,423,773 A | * | 6/1995 | Jimenez ..................... 604/282 |
| 5,454,795 A | * | 10/1995 | Samson ..................... 604/282 |
| 5,531,715 A | | 7/1996 | Engelson et al. .......... 604/265 |
| 5,538,512 A | | 7/1996 | Zenzon et al. ............. 604/280 |
| 5,545,151 A | | 8/1996 | O'Connor et al. ......... 604/282 |
| 5,603,721 A | * | 2/1997 | Lau et al. ................... 606/195 |
| 5,630,806 A | | 5/1997 | Inagaki et al. ............. 604/282 |
| 5,658,264 A | * | 8/1997 | Samson ..................... 604/282 |
| 5,676,659 A | * | 10/1997 | McGurk .................... 604/282 |
| 5,695,483 A | | 12/1997 | Samson ..................... 604/282 |
| 5,702,373 A | * | 12/1997 | Samson ..................... 604/282 |
| 5,728,063 A | * | 3/1998 | Preissman et al. ............ 604/96 |
| 5,782,811 A | * | 7/1998 | Samson et al. ............. 604/282 |
| 5,827,201 A | * | 10/1998 | Samson et al. ............. 600/585 |
| 5,836,926 A | | 11/1998 | Peterson et al. ............ 604/282 |
| 5,891,114 A | * | 4/1999 | Chien et al. ................ 604/282 |
| 5,906,606 A | * | 5/1999 | Chee et al. ................. 604/527 |

FOREIGN PATENT DOCUMENTS

| | | | |
|---|---|---|---|
| EP | 0369383 | 5/1990 | .......... A61M/25/00 |
| EP | 0420993 | 4/1991 | .......... A61M/25/00 |
| EP | 0421650 | 4/1991 | .......... A61M/25/00 |
| EP | 0594201 | 4/1994 | .......... A61M/25/00 |
| EP | 0643979 | 3/1995 | .......... A61M/25/00 |
| EP | 0732117 | 9/1996 | .......... A61M/25/00 |
| EP | 9633763 | 10/1996 | .......... A61M/25/00 |
| FR | 2613231 | 4/1987 | .......... A61M/23/00 |
| JP | 2283346 | 11/1990 | .......... A61B/1/00 |
| JP | 3023830 | 1/1991 | .......... A61B/1/00 |
| JP | 0556910 | 3/1993 | .......... A61M/1/00 |
| JP | 5220225 | 8/1993 | .......... A61M/25/00 |
| WO | 9207507 | 5/1992 | .......... A61B/5/00 |
| WO | 9305842 | 4/1993 | .......... A61M/29/02 |
| WO | 9315785 | 8/1993 | .......... A61M/25/00 |
| WO | 9513110 | 5/1995 | .......... A61M/25/00 |
| WO | 0110492 | 2/2001 | .......... A61M/25/00 |

* cited by examiner

REDUCED PROFILE DELIVERY SYSTEM

This application claims the benefit of priority based on Provisional Application No. 60/147,645 entitled "Reduced Profile Delivery System," filed Aug. 6, 1999.

BACKGROUND OF THE INVENTION

The present invention relates to body insertable catheters and other tubular treatment devices, and more particularly to the manner in which such devices can be reinforced with metallic wires or strands.

Procedures involving entry into or treatment of body lumens, e.g., intravascular treatment procedures, frequently employ catheters. A variety of catheter types have been developed to meet different treatment needs. For example, U.S. Pat. No. 4,547,193 discloses an angiographic catheter. U.S. Pat. No. 5,364,357 discloses a small diameter coronary angioplasty catheter, more particularly a balloon dilatation catheter for expanding vascular passages. U.S. Pat. No. 5,221,270 is drawn to a soft tip guiding catheter, which, after its insertion into a body lumen, is used to receive other devices and guide them through the same lumen. U.S. Pat. No. 5,026,377 discloses a catheter used to deploy and position a self-expanding stent in a body lumen.

The variety of uses notwithstanding, certain properties are necessary or desirable, regardless of the catheter type. All catheters must be biocompatible, with vascular catheters further requiring hemocompatibility. To varying degrees, catheters require sufficient axial strength to facilitate movement of the catheter distal end through vascular passages or other body lumens by applying an axial pushing force near the catheter proximal end. This characteristic is often called "pushability." A related characteristic, "torqueability," refers to the ability to rotate the catheter distal end by rotating its proximal end. Torqueability is useful, for example, in using a helical fixation member to temporarily or permanently secure a catheter to tissue. Flexibility, particularly along a distal end region of the catheter, becomes increasingly important as the catheter enters more serpentine or tortuous passages. Another characteristic that becomes more important with increased curvature of passages is the capacity to resist kinking, sometimes referred to as "kinkability."

The quest to provide treatment options for narrower vessels and other lumens has given rise to the need to reduce catheter sizes, yet retain their favorable structural properties. One successful approach involves providing a metal reinforcement layer within a polymeric catheter body. While several of the aforementioned patents concern this approach, reference also is made to U.S. Pat. No. 5,836,926 (Peterson, et al.), disclosing an intravascular catheter that incorporates a reinforcing layer of interbraided stainless steel wires. The reinforcing layer is situated between an inside layer of polytetrafluoroethylene, and an outer layer comprising a blend of polyetherester elastomer and polybutylene terepthalate. As compared to a similarly sized catheter without the metallic reinforcement, this catheter can achieve improved pushability and torqueability, as well as improved kink resistance, while remaining sufficiently flexible.

In catheters used to deliver stents or other prostheses (e.g., grafts), a reduction in catheter diameter limits the prostheses deliverable by the device to smaller diameter prostheses, or alternatively increases the degree of radial compression applied to a prosthesis to enable its delivery. For a radially self-expanding prosthesis, the increased radial compression also increases the radial force between the prosthesis and surrounding catheter when the prosthesis is in its reduced-radius delivery state. The increase in radial force causes a proportionate increase in the frictional force that interferes with deployment of the prosthesis after its delivery to the treatment site.

To achieve further reductions in diameter of a metallic-braid-reinforced catheter, the thickness of the polymeric wall might be reduced, either with or without reducing the size of the wires or strands of the metal reinforcement. However, reducing the diameters of the strands reduces their strength, and thus diminishes one or more of the properties associated with strength: pushability, torqueability and kink resistance. Reducing the polymeric wall thickness while maintaining the strand size, however, eventually leads to unwanted exposure of the reinforcing braid.

Therefore, it is an object of the present invention to provide a catheter or other tubular medical device with a structure that, despite a reduction in diameter, maintains favorable properties related to the strength of a reinforcing strand. Another object is to provide a catheter structure that affords enhanced capacity to control desired properties.

A further object is to provide a process for fabricating a catheter that either enhances desired properties, or retains desired properties at acceptable levels despite a reduced diameter.

Yet another object is to provide a prosthesis delivery catheter capable of accommodating larger prostheses, or that requires less radial compression of a prosthesis during its delivery to a designated treatment site within a body lumen.

SUMMARY OF THE INVENTION

To achieve these and other objects, there is provided a body insertable medical device. The device includes a pliable tubular body having an inside surface, an outside surface, and a wall thickness in a radial direction. The tubular body surrounds an interior lumen. The device further includes a reinforcing structure including at least one elongate flexible structural strand having a substantially uniform non-circular transverse profile. The profile has a thickness dimension and a width dimension at least twice the thickness dimension. The structural strand is incorporated into the tubular body between the outside surface and the inside surface in a substantially surrounding relation to the interior lumen. The structural strand is oriented with the thickness dimension in the radial direction.

Preferably a plurality of the structural strands are wound helically in opposite directions and interbraided with one another, to form multiple crossings of the structural strands. The strands are spaced apart axially to define multiple pics. The axial length of the pics, as determined by the strand spacing, can be selected to influence pushability, torqueability, flexibility and kink resistance. The transverse profiles of the strands, both as to surface area and as to the ratio of width to thickness, also can be selected to influence these characteristics. For example, structural strand strength can be increased by increasing the strand width while maintaining the same thickness. Flexibility can be increased by increasing the pic axial length. Another factor influencing the desired characteristics is the braid angle of the filament strand windings, i.e., the angle of each helical strand with respect to a longitudinal central axis. Increasing the braid angle tends to increase the torqueability while reducing the pushability. In short, strands and arrangements of strands can be selected to customize catheter designs, to an extent not possible in braids formed of the conventional strands having circular profiles.

In one particularly preferred construction, the strands have rectangular transverse profiles, with width-to-thickness ratios in the range of 3.0 to 6.6.

In a specific example, a stainless steel braid features structural strands having a rectangular transverse profile in which the width is 0.003 inches, and the thickness is 0.0007 inches. This arrangement maintains the desired pushability, torqueability and kink resistance, e.g., as compared to a braid employing conventional strands having circular transverse profiles with 0.003 inch diameters. Further, satisfactory flexibility results from a pic rate of about 80–100 pics per inch, i.e., a pic axial length in the range of 0.01 inches to 0.0125 inches.

In one advantageous construction, the tubular body comprises an inside layer formed of a low-friction polymeric material, and an outside layer surrounding the inside layer and formed of a polyether ester or a polymeric amide. The structural strand reinforcement is situated between the inside layer and the outside layer. The inside layer provides lubricity, i.e., reduced friction to ease the deployment of a stent or otherwise facilitate passage of any member within the interior lumen. The outer layer can be composed of a distal section to enhance distal end flexibility, and a less flexible proximal section to enhance pushability and kink resistance.

According to another aspect of the invention there is provided a process for fabricating a catheter, including:
a. positioning a polymeric inner tube over an assembly mandrel;
b. selecting an elongate flexible structural strand having a non-circular transverse profile characterized by a thickness dimension and width dimension at least twice the thickness dimension;
c. winding the structural strand helically over a core rod, with the thickness dimension oriented radially with respect to the core rod, thus to form a tubular support structure;
d. removing the tubular support structure from the core rod, and placing the support structure over the polymeric inner tube and assembly mandrel;
e. placing a polymeric outer tube over the tubular support structure, whereby the polymeric outer tube surrounds the polymeric structure and the inner polymeric tube;
f. placing a heat shrink tube around the polymeric outer tube to form an assembly including the heat shrink tube, the polymeric outer tube, the tubular support structure and the polymeric inner tube;
g. applying heat to the assembly sufficient to cause a radial shrinkage of the heat shrink tube, thereby radially compressing the assembly;
h. heating the radially compressed assembly sufficiently to form a fusion bond along an interface of the polymeric inner and outer tubes; and
i. after forming the fusion bond, removing the heat shrink tube.

Thus, in accordance with the present invention, catheters with metal reinforcement can be formed with reduced diameters, yet retain favorable pushability, torqueability and resistance to kinking. These characteristics, along with flexibility, can be more precisely tailored to meet varying needs. Catheters used to deploy stents and other prostheses can be fashioned to handle prostheses of larger sizes, or to require a less severe radial contraction of a radially self-expanding prosthesis to achieve its delivery state. Alternatively, a catheter can be fashioned with the same prosthesis delivery capacity as a conventional catheter, but with a reduced diameter.

IN THE DRAWINGS

For a further understanding of the above and other features and advantages, reference is made to the following detailed description and to the drawings, in which.

DETAILED DESCRIPTION OF THE PREFERRED EMBODIMENTS

Figure 1:
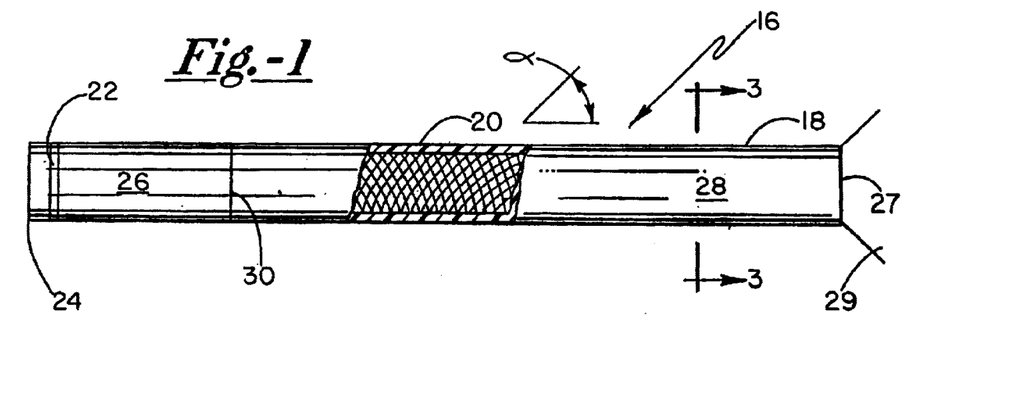
FIG. 1 is a side elevation of a prosthesis delivery and deployment device constructed in accordance with the present invention.
Figure 2:
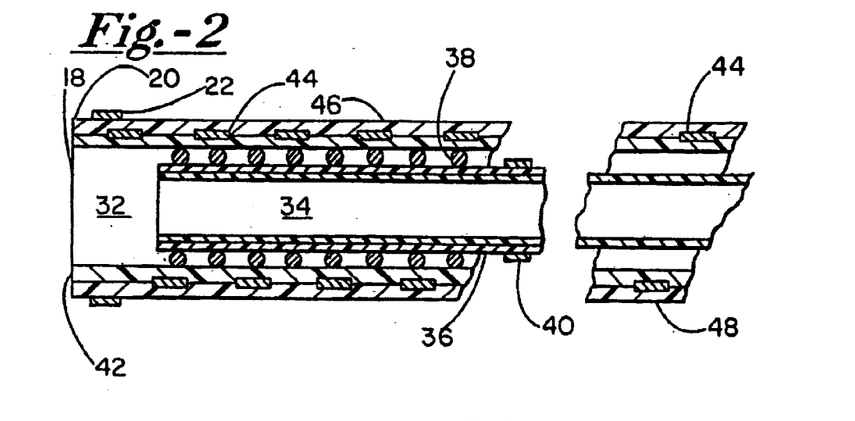
FIG. 2 is an enlarged elevation, partially sectioned to show further features of the device.

Turning now to the drawings, there is shown a device 16 for delivering a radially self-expanding prosthesis to a selected treatment site within a body cavity or body lumen, and for deploying the prosthesis, once it is positioned at the treatment site. The device includes an elongate, flexible outer catheter 18 having a tubular catheter wall 20. A radiopaque marker 22 is mounted to the catheter near its distal end 24.

Along its axial length, catheter wall 20 is divided into two regions: a distal region 26 and a proximal region 28. As indicated by the break, the full length of proximal region 28 is not shown. Typically, the proximal region is considerably longer than the distal region. A distal end 27 of the catheter is joined to a hub 29.

Distal region 28 extends from distal end 24 to a junction 30 between two slightly different polymeric materials employed in forming the catheter wall. Along the distal region, the catheter wall preferably is more flexible, to enhance the capability of the catheter to negotiate serpentine or tortuous vascular passages. Along proximal region 28, the catheter preferably is less flexible to provide enhanced axial and circumferential strength, for enhanced pushability and torqueability, respectively. The device also must exhibit resistance to kinking along its entire length.

FIG. 2 shows device 16 in greater detail. Outer catheter 18 includes a catheter lumen 32 that runs substantially the entire catheter length. An inner catheter 34, contained in the lumen, is moveable axially relative to the outer catheter. Inner catheter 34 extends lengthwise substantially along the entire length of the outer catheter. A sleeve 36 surrounds the inner catheter along a distal portion of the catheter comparable to catheter distal region 26 in its axial length. A prosthesis, in particular a radially self-expanding stent 38, surrounds the inner catheter and sleeve along the distal portion of the inner catheter. Stent 38 in turn is surrounded by the distal region of the outer catheter, constrained by the outer catheter wall in a radially reduced, axially elongated state. Stent 38 is radially self-expanding, in that as the stent is removed from the outer catheter, it tends to shorten axially and expand radially to a normal or unstressed state in which the stent diameter is larger than the diameter of the outer catheter. Stent 38 is composed of oppositely directed helically wound filaments or wires that intersect one another. A radiopaque marker 40 is located along inner catheter 34, between the inner catheter and the sleeve.

As best seen in FIG. 2, catheter wall 20 has a layered construction including an inner layer or liner 42 that extends for the length of the catheter. Liner 42 is formed of a material selected to provide high lubricity (low friction), e.g., polytetrafluoroethylene (PTFE). Polyethylene also may be used.

Surrounding the inner layer is a reinforcing braid formed of multiple flexible elongate strands or wires 44, helically wound about the liner and interbraided with one another to form multiple crossings or intersections. Strands 44 can be formed of stainless steel, e.g., 304V stainless steel having a tensile strength of about 338 ksi. Other high tensile strength materials can be used, e.g., a cobalt-based alloy sold under the brand name Elgiloy. The braid reinforcement extends along the entire length of device 16, although in certain applications it may be desirable to provide a distal end region that does not incorporate the braid.

An outer layer surrounds the reinforcement braid, and is provided in the form of a distal outer tube 46 and a proximal outer tube 48. Strands 44 are embedded within the catheter wall, such that the wall thickness is determined substantially by the combined thicknesses of liner 42 and outer tube 46. Likewise, the wall thickness along proximal region 28 is determined by the thicknesses of liner 42 and tube 48. Depending on the method of fabrication, strands 44 are embedded substantially equally in both the liner and the outer layer, or alternatively are embedded substantially within the outer layer. Outer layers 46 and 48 abut one another at junction 30, and are bonded to the inner liner. Consequently, the liner, outer layers and reinforcing braid are integral with one another.

Outer layers 46 and 48 are preferably formed of a polyester ether, e.g., a homopolymer sold under the brand name Arnitel, or a polymeric amide such as a nylon copolymer sold under the brand name Pebax. Further, however, different polymers are advantageously used to provide different degrees of flexibility in distal region 26 and proximal region 28. In particular, outer layer 46 can be formed of a polyester or nylon having a 63D hardness, while proximal outer layer 48 is formed of a material having a higher hardness, and therefore reduced flexibility but increased torqueability, pushability and resistance to kinking.

Figure 3:
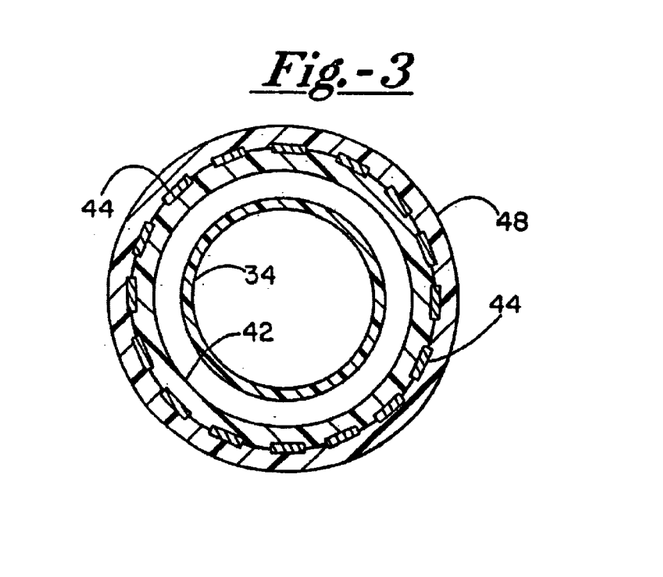
FIG. 3 is a sectional view taken along the line 3—3 in FIG. 1.

In particular versions of device 16, namely a "6 French" device and a "7 French" device, the catheter wall thickness is about 0.004–0.005 inches, including liner 42 of about 0.001 inches thick and outer layers 46 and 48 at a thickness of 0.003–0.004 inches. Strands 44 have rectangular transverse profiles, with a thickness of 0.0007 inches ±0.002 inches and a width of 0.003 inches±0.0003 inches. The catheter wall 20 is reduced in thickness, largely due to a reduction in strand thickness to 0.0007 inches, as compared to a 0.003 "thickness" of a conventional 0.003 inch diameter strand or wire. The reduced strand thickness allows a reduced thickness in catheter wall 20 without encountering unwanted strand exposure. As a result, the 6 French version of the device has an outer diameter of 0.0790 inches, with an inner diameter enlarged to 0.0690 inches. The 7 French device outer and inner diameters are 0.0920 inches and 0.0780 inches, respectively.

The permitted reduction in outer diameter, or the permitted increase in internal diameter, actually is more than a direct comparison of the rectangular and circular strand might suggest. First, the impact of the thickness reduction is doubled because the overall diameter incorporates two thicknesses of the catheter wall. A further doubling occurs when the crossings or intersections of strands are taken into account.

Figure 4:
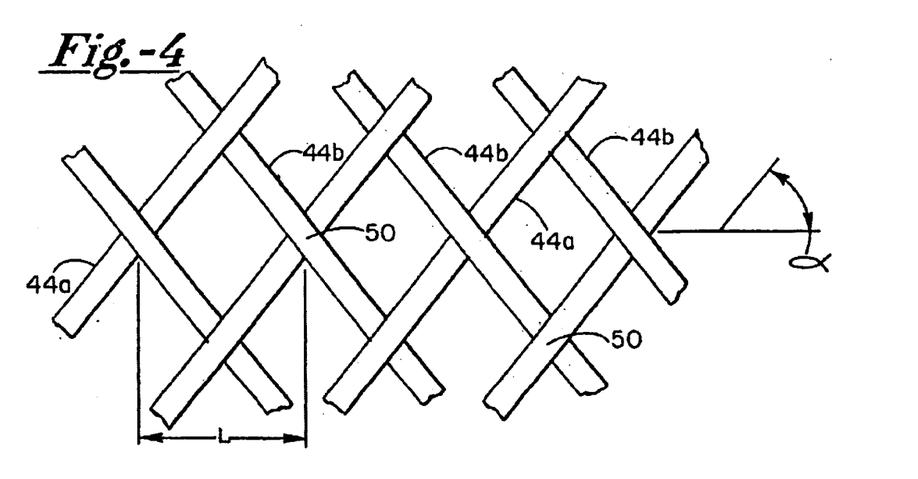
FIG. 4 is a schematic view of the braid pattern in which structural strands reinforcing the device are arranged.

FIG. 4 illustrates several strands 44a and 44b wound helically in respective first and second directions, and interbraided in a 1-over-1-under braid pattern. Alternate patterns, e.g., 2-over-2-under, can be used. In any event, the strands form multiple crossings or intersections 50, each involving one strand 44a and one strand 44b. The axial spacing between adjacent strands in both directions is substantially uniform. As a result, strands 44a and 44b cooperate to form multiple diamond or rhombic "pics" of substantially uniform size, particularly as to axial length L. The pic size also can be considered in terms of a rate of pics per inch. Specifically, a pic rate of 80–100 pics per inch determines a pic axial length range of 0.010–0.0125 inches. The 80–100 pic rate has been found to provide satisfactory performance characteristics in both the 6 French and 7 French versions of the device.

Figure 5:
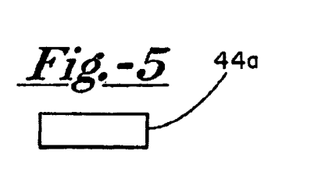
FIG. 5 is an enlarged view of a structural strand transverse profile.

FIG. 5 shows an enlarged transverse profile of one of strands 44a. Strands 44b have substantially the same transverse profiles as to size and shape. As noted above, the rectangular profile affords the advantage of maintaining favorable catheter characteristics that depend on strand strength, yet reducing the required thickness of the catheter wall. While the advantage can be realized to an extent if the width is at least twice the thickness, more preferably the ratio of strand width dimension to strand thickness dimension is at least 3, more preferably in a range of 3.0–6.6.

Figure 6:
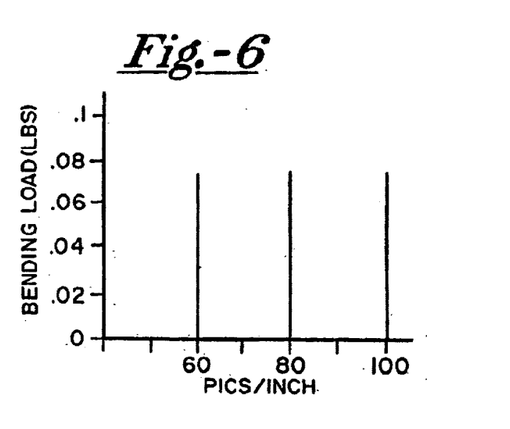
FIG. 6 is a graph illustrating distal end flexibility of the device as a function of pic rate.

FIG. 6 is a graph illustrating the flexibility of distal region 26 in terms of the force required to bend the device, with a higher bending force representing reduced flexibility. The test was conducted with a self-expanding stent in the reduced-radius delivery state, maintained within interior lumen 32. The results indicate that varying the pic rate from 60 pics per inch to 100 pics per inch have negligible impact on flexibility.

Figure 7:
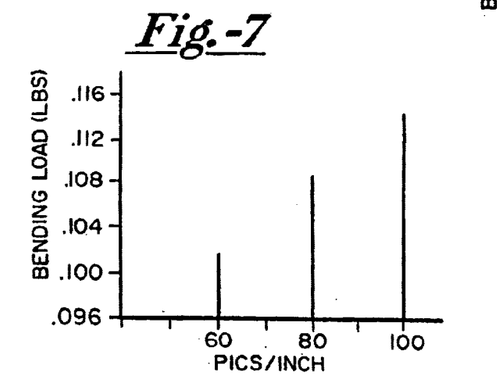
FIG. 7 is a graph illustrating flexibility of a proximal region of the device as a function of pic rate.

In contrast, varying the pic rate over the same range along proximal region 28 has a definite impact on flexibility, as indicated in the graph of FIG. 7. In particular, the 6 French and 7 French versions of the device were found to have an undesirably high flexibility, and low kink resistance, when formed at a pic rate of 60 pics per inch. A pic rate of 80–100 pics per inch provided sufficient kink resistance while retaining sufficient flexibility. Further, flexibility was found to remain substantially stable, despite increases in the pic rate above 100 pics per inch, although this is not illustrated in FIG. 7.

Figure 8:
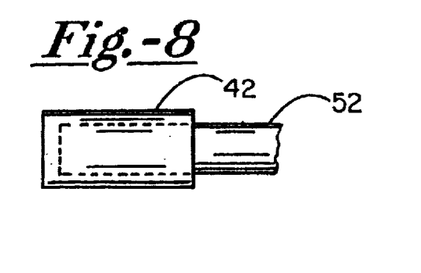
FIGS. 8–13 schematically illustrate fabrication of the device.
Figure 9:
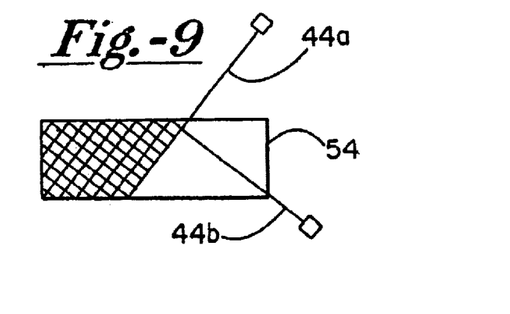

FIGS. 8–13 illustrate one approach to manufacturing device 16. As seen in FIG. 8, an initial step involves placing a PTFE inside tube or liner 42 over an assembly mandrel 52. The assembly mandrel is selected based on the required inner diameter of the catheter. Next, strands 44 are wound onto a core rod 54 at a desired braid angle, axial spacing and braiding pattern. Adequate spring tension is placed on each braid spool to maintain the desired pattern. One preferred embodiment of the process involves interbraiding 16 strands, although the number of strands can be varied to suit different needs. The braider also is configured to provide a desired pic rate, e.g., 90 pics per inch.

Figure 10:
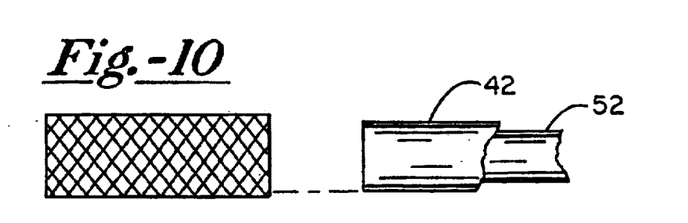

After braiding, the reinforcement braided structure is removed from core rod 54 and placed around inside tube 42 on mandrel 52, as shown in FIG. 10.

Figure 11:
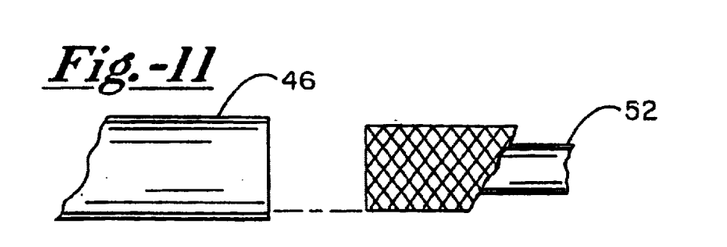
Figures 12, 13:
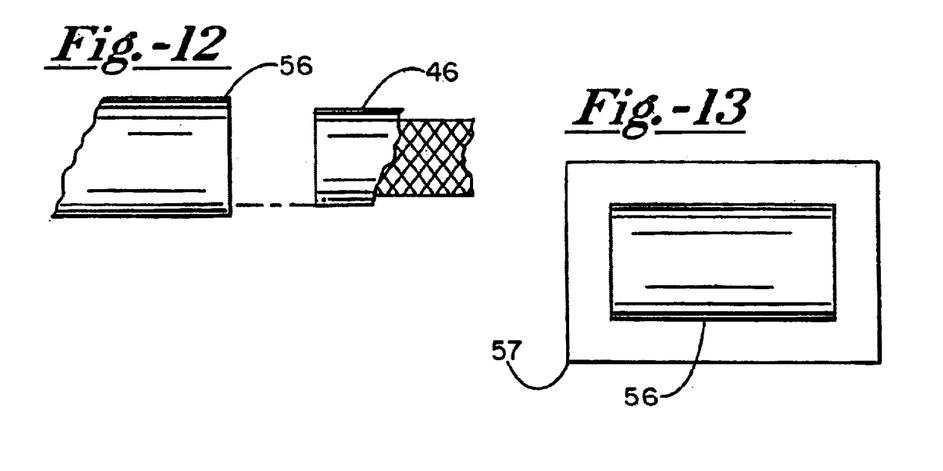
Figure 14A:
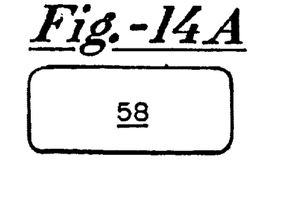
FIGS. 14a–d illustrate alternative structural strand profiles.
Figure 14B:
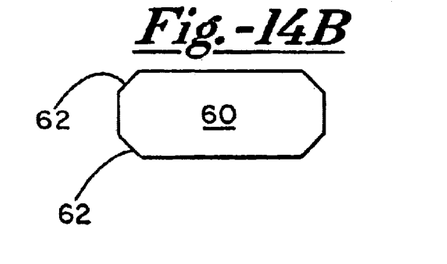
Figure 14C:
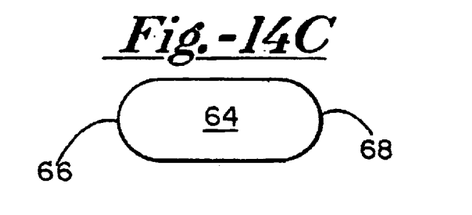
Figure 14D:
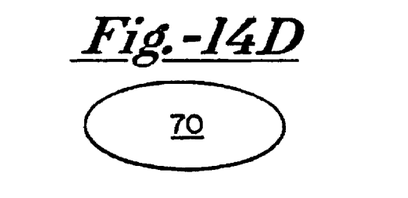

Next, an outside tube 46/48 is positioned around the braid (FIG. 11). A heat shrink tube 56 is placed around the outside tube, to provide an assembly including the outside tubes, the reinforcement braid and the inside tube, along with the heat shrink tube, as seen in FIG. 12. Heat is applied at a low rate, sufficient to cause the heat shrinkable tube 56 to shrink radially, thus to radially compress the remainder of the assembly. The radial compression of the assembly brings the outside tube and the inside tube more closely together, so that they are contiguous along an interface and cooperate to substantially surround or embed the reinforcing strands.

Finally, as seen in FIG. 13, the radially compressed assembly is heated in a convection oven 57 at a considerably higher temperature (e.g., in the range of 300–500 degrees F., which causes outside tube 46/48 and inside tube 42 to form a fusion bond along their interface.

After the heat fusion and cooling of the assembly, the heat shrink tubing is cut and removed, yielding the completed catheter. In many cases there is a final step of etching a portion of exposed braid at the catheter distal end.

In an alternative fabrication process (not illustrated), the PTFE inside tube is placed over a copper core, after which the structural strands are braided onto the tube/core assembly. After braiding, an outer layer is applied by extrusion over and around the inside tube/braid assembly at a constant rate. The copper core shrinks when cooled, facilitating removal of the catheter.

The device has been found to exhibit satisfactory performance characteristics despite the reduced wall thickness enabled by the non-circular structural strands. For example, axial force (pushability) through a representative model was achieved by applying a force considerably less than the permitted maximum of 4.0 pounds at 37 degrees C., while avoiding kinking of the device. Stent deployment and recapture forces likewise were considerably less than the required maximum allowable values. The tensile strength of the catheter/valve body connection exceeded the required minimum. Finally, kink resistance exceeded requirements. More particularly, with a device expected to pass through a 3.0 inch arc successfully without kinking, the present devices were able to pass through a 2.0 inch radius arc, thus exceeding the requirement.

As noted above, a variety of factors can be selectively varied to obtain desired performance characteristics, including the strand width and thickness, the braid pattern, axial spacing between strands, and braid angle. The braid angle, illustrated at α in FIGS. 1 and 4, is the angle between the helical braid and the central axis of the braid, projected onto a plane containing the central axis, e.g., the plane of FIG. 1. Increasing the braid angle tends to enhance torqueability, while reducing the braid angle tends to enhance pushability.

FIGS. 14*a*–*d* illustrate alternative embodiment structural strands with different transverse profiles, including a strand 58 with rounded corners, a strand 60 with beveled corners or edges 62, a strand 64 with rounded opposite sides 66 and 68, and a strand 70 with a substantially elliptical profile. In all cases, a width or major diameter preferably is in the range of 3.0–6.6 times the thickness or minor diameter.

Figure 15:
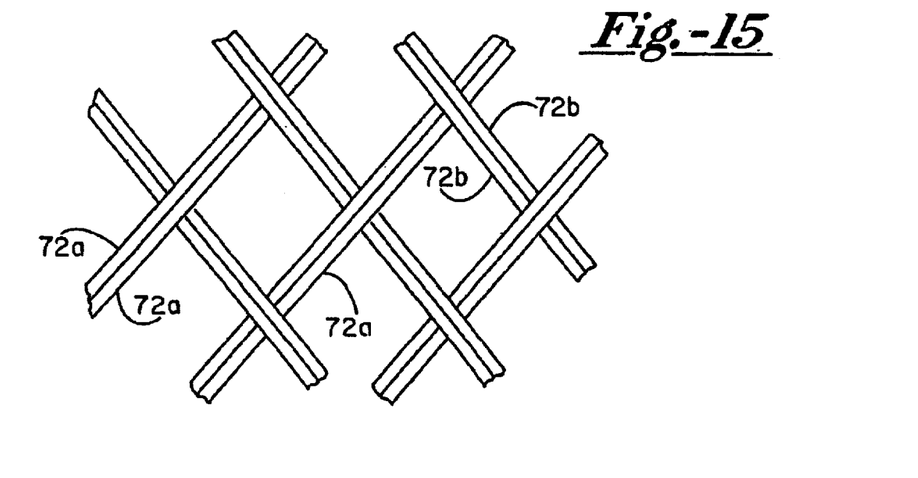
FIG. 15 illustrates a braid pattern of an alternative embodiment device.
Figure 16:
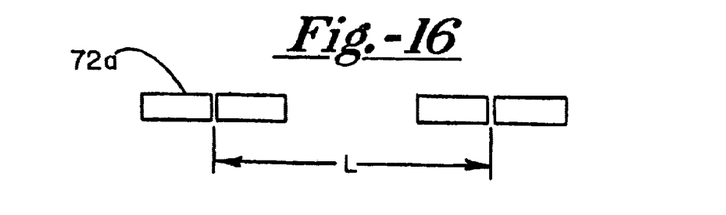
FIG. 16 is a sectioned view of the alternative embodiment structural strand arrangement.

FIGS. 15 and 16 illustrate an alternative embodiment reinforcing arrangement in which helically woven strands 72*a* and 72*b* are arranged in pairs of strands, with adjacent pairs spaced apart axially from one another. The distance "L" in FIG. 16 illustrates the axial spacing between two pairs of strands, and thus also indicates an axial length of the pics formed in this alternative arrangement. Each strand 72*a* or 72*b* has a width of about 1.5 times its thickness. As a result, the side-by-side pair of strands has the given thickness, in combination with an effective width about three times the thickness. The strands could be arranged in sets of three or more side-by-side strands, if desired. Providing strands in sets can provide the aforementioned advantages, with an increase in flexibility as compared to the previous embodiment.

Thus, in accordance with the present invention, the outside diameter of a catheter can be reduced without a corresponding reduction in the diameter of its interior lumen, to facilitate use of the catheter in smaller diameter vascular passages and other body lumens. Alternatively, the size of a catheter's interior lumen may be increased without enlarging the catheter itself, thus to accommodate an increased fluid flow or a larger inner catheter or stent. Alternatively, the larger interior lumen can deliver a stent radially compressed to a lesser degree, reducing the radial elastic restoring force, thereby reducing friction to facilitate stent deployment.

What is claimed is:

1. A catheter, including:

a pliable tubular catheter body having an inside surface, an outside surface, and a wall thickness in a radial direction, said tubular catheter body surrounding an interior lumen, and having a proximal body section and a distal body section more flexible than the proximal body section; and a plurality of elongate flexible structural strands integral with the catheter body and helically wound in first and second opposite directions in surrounding relation to the interior lumen to provide a reinforcing arrangement for strengthening the tubular catheter body, said reinforcing arrangement extending axially along the proximal body section and the distal body section with adjacent windings of the strands in each of the first and second directions being spaced apart axially to determine multiple pics having a substantially uniform axial pic length over the axial length of the reinforcing arrangement; and wherein the structural strands have a substantially uniform transverse profile including a strand thickness and a strand width at least twice the strand thickness, and the structural strands are oriented with the respective strand thicknesses in the radial direction and with the respective strand widths normal to the radial direction.

2. The catheter of claim 1 wherein:

the substantially uniform axial pic length is in the range of from about 0.01 inches to about 0.025 inches.

3. The catheter of claim 1 wherein:

the structural strands are interbraided with one another.

4. The catheter of claim 1 wherein:

said transverse profile of the structural strands is rectangular.

5. The catheter of claim 1 wherein:

the structural strands are formed of a metal.

6. The catheter of claim 1 wherein:

the structural strands are incorporated into the tubular catheter body between the outside surface and the inside surface.

7. The catheter of claim 6 wherein:

the catheter body comprises an inside layer and an outside layer surrounding the inside layer.

8. The catheter of claim 7 wherein:

the structural strands are substantially embedded in at least one of the inside and outside layers.

9. The catheter of claim 7 wherein:

the inside layer is formed of a low-friction polymeric material selected from the group consisting of: polytetrafluoroethylene (PTFE) and polyethylene.

10. The catheter of claim 7 wherein:

the outside layer is formed of at least one constituent selected from the group consisting of: polyether esters and polymeric amides.

11. The catheter of claim 10 wherein:

the at least one constituent is selected from the group consisting of: nylon copolymers and polyester homopolymers.

12. The catheter of claim 7 wherein:

the outside layer comprises a distal outside layer section corresponding to the distal body section, and a proximal outside layer section corresponding to the proximal body section, and the distal outside layer section is more flexible than the proximal outside layer section.

13. The catheter of claim 12 wherein:

a distal end of the distal outer layer section coincides with a distal end of the inside layer.

14. The catheter of claim 7 wherein:

the elongate flexible structural strands are disposed between the inside layer and the outside layer.

15. The catheter of claim 7 wherein:

the distal outside layer section is formed of a first constituent, and the proximal outside layer section is formed of a second constituent having a hardness higher than that of the first constituent.

16. The catheter of claim 7 wherein:

the distal outer layer section is more flexible than the proximal outer layer section.

17. The catheter of claim 7 wherein:

the proximal outer layer section has more axial strength and more circumferential strength than the distal outer layer section.

18. The catheter of claim 7 wherein:

the inner layer, the outer layer, and the reinforcing arrangement are integral with one another.

19. The catheter of claim 1 wherein:

the elongate flexible structural strands are substantially uniform in composition over the axial length of the reinforcing arrangement.

20. The catheter of claim 1 wherein:

the elongate flexible structural strands are encased within the pliable tubular catheter body.

* * * * *